United States Patent [19]

Goddard

[11] 4,258,060
[45] Mar. 24, 1981

[54] SUBSTITUTED TRICHLOROPROPYLUREAS AS PLANT DISEASE CONTROL AGENTS

[75] Inventor: Steven J. Goddard, West Grove, Pa.

[73] Assignee: E. I. Du Pont de Nemours and Company, Wilmington, Del.

[21] Appl. No.: 65,864

[22] Filed: Aug. 13, 1979

[51] Int. Cl.$^3$ .................... A01N 37/20; A01N 37/18; C07C 103/38; C07C 127/00
[52] U.S. Cl. ................................. 424/322; 424/300; 424/320; 560/160; 560/165; 564/60; 564/224
[58] Field of Search ...................... 260/553 R, 561 R; 424/300, 320, 322; 560/160, 165

[56] References Cited

U.S. PATENT DOCUMENTS 4,111,683   9/1978   Singer ................................. 560/165

Primary Examiner—Richard Raymond

[57] ABSTRACT

Substituted trichloropropylureas such as 1-(1,1-dimethylethyl)-3-methyl-(3,3,3-trichloro-2-hydroxypropyl)urea are useful in controlling plant fungus diseases.

9 Claims, No Drawings

SUBSTITUTED TRICHLOROPROPYLUREAS AS PLANT DISEASE CONTROL AGENTS

BACKGROUND OF THE DISCLOSURE

This invention relates to substituted trichloropropylureas, and, more particularly, to substituted trichloropropylureas such as 1-(1,1-dimethylethyl)-3-methyl-(3,3,3-trichloro-2-hydroxypropyl)urea which are useful in controlling diseases of living plants.

No prior art is known to exist which would make synthesis and use of the compounds of this invention obvious.

SUMMARY OF THE INVENTION

The present invention resides in the discovery that compounds of the Formula (I)

$$\text{(I)}$$

wherein
$R^1$ is $CH_3NH$, $CH_3O$, or $CH_3$;
$R^2$ is $CH_3$ or $H\equiv C$; and
$R^3$ is H or $$CH_3NH\overset{O}{\underset{\|}{C}}-$$

provided that when $R^2$ is $HC\equiv C$, $R^1$ is $CH_3NH$ and $R^3$ is H;
and provided that when $R^3$ is $$CH_3NH\overset{O}{\underset{\|}{C}}-,$$

$R^1$ is $CH_3NH$ and $R^2$ is $CH_3$;
are effective plant disease control agents.

This invention also relates to compositions in which the compounds of this invention are an active ingredient and to methods of using the compounds to control plant diseases.

DETAILED DESCRIPTION OF THE INVENTION

PREPARATION:

The compounds of this invention can be prepared as shown in the following reaction sequence:

Step 1

Step 1

The preparation of 2-(trichloromethyl)oxirane is reported by H. Gilman and R. K. Abbott, Jr., *J. Org. Chem.* 8, 224 (1943). 2-(Trichloromethyl)oxirane can be reacted with 1,1-dimethylethylamine at about −30° to +50° C. in a solvent such as methanol to produce 3-(1,1-dimethylethylamino)-1,1,1-trichloro-2-propanol.

Step 2

The reaction of 3-(1,1-dimethylethylamino)-1,1,1-trichloro-2-propanol with methyl isocyanate normally takes place at −70° to +80° C. in an inert solvent such as chloroform to produce 1-(1,1-dimethylethyl)-3-methyl-1-(3,3,3-trichloro-2-hydroxypropyl)urea and 1-(1,1-dimethylethyl)-3-methyl-1-[3,3,3-trichloro-2-(methylcarbamoyloxy)propyl]urea.

Step 3

3-(1,1-Dimethylethylamino)-1,1,1-trichloro-2-propanol can then be reacted with methyl chloroformate at about −70° to +70° C. in the presence of an acid acceptor such as triethylamine in a solvent such as dichloromethane to produce methyl (1,1-dimethylethyl)-(3,3,3-trichloro-2-hydroxypropyl)carbamate.

Step 4

The reaction of 3-(1,1-dimethylethylamino)-1,1,1-trichloro-2-propanol with acetic anhydride takes place at about −70° to +70° C. in a solvent such as dichloromethane to produce the N-(1,1-dimethylethyl)-N-(3,3,3-trichloro-2-hydroxypropyl)acetamide of this invention.

The preparation of the compounds of this invention is further illustrated by the following examples.

EXAMPLE 1

To 200 grams of stirred methanol were added 48.4 grams of 2-(trichloromethyl)oxirane and 21.9 grams of 1,1-dimethylethylamine at equimolar rates, dropwise, at 20° C. during 30 minutes. After stirring 16 hours at ambient temperature, the solvent was removed under reduced pressure of 100 mm. Hg and the white residue recrystallized from 300 grams of hexane to yield 50.7 grams of 3-(1,1-dimethylethylamino)-1,1,1-trichloro-2-propanol melting 100.5°–102° C.

The following compound was prepared by replacing 1,1-dimethylethylamine with 1,1-dimethyl-2-propyn-1-amine in Example I: 2-[(1,1-dimethyl-2-propynyl)amino]-1-(trichloromethyl)ethanol, m.p. 48°–50° C.

EXAMPLE 2

To a refluxing solution of 5 grams of 3-(1,1-dimethylethylamino)-1,1,1-trichloro-2-propanol and 0.1 gram of dibutyldihydroxytindidodecanoate in 50 grams of chloroform, 2.51 grams of methyl isocyanate was added dropwise during 10 minutes. After refluxing 1 hour, the reaction mixture was evaporated under reduced pressure of 100 mm. Hg to 7.75 grams of a glass. Crystallization of this glass from hexane gave 3.1 grams of white crystals which were recrystallized from a mixture of 10 grams of hexane and 3 grams of toluene to yield 2.7 grams of white 1-(1,1-dimethylethyl)-3-methyl-1-(3,3,3-trichloro-2-hydroxypropyl)urea melting 141.5°–142.5° C. The filtrate from the original crystallization was evaporated under reduced pressure of 100 mm. Hg. to a glass which was crystallized from hexane to yield 2.7 grams of white 1-(1,1-dimethylethyl)-3-methyl-1-[3,3,3-trichloro-2-(methylcarbamoyloxy)propyl]urea melting 119°–123° C.

EXAMPLE 3

Twenty milliliters of a 1 M dichloromethane solution containing 1.17 grams of methylisocyanate was added dropwise to a stirred suspension of 5 grams of 2-[(1,1-dimethyl-2-propynyl)amino]-1-(trichloromethyl)ethanol at −70° C. during 15 minutes. The reaction mixture was allowed to warm to ambient temperature during 1 hour and then stirred for 3 hours. The reaction mixture was evaporated under a reduced pressure of 100 mm. Hg to give 7.7 grams of a white solid which was recrystallized from 25 grams of 1-chlorobutane and 10 grams of hexane to yield 2.9 grams of off-white N-(1,1-dimethyl-2-propynyl)-N'-methyl-N-(3,3,3-trichloro-2-hydroxypropyl)urea melting 120.0°–120.5° C.

EXAMPLE 4

To a stirred solution of 5 grams of 3-(1,1-dimethylethylamino)-1,1,1-trichloro-2-propanol and 2.15 grams of triethylamine in 50 grams of dichloromethane, cooled to −60° C., 2.01 grams of methylchloroformate was added dropwise during 5 minutes. After allowing the reaction mixture to warm to ambient temperature during 1 hour, the mixture was stirred for 3 hours. The reaction mixture was evaporated under a reduced pressure of 100 mm. Hg to 5.6 grams of an oil which was crystallized from 50 grams of hexane to yield 5.2 grams of white methyl (1,1-dimethylethyl)-(3,3,3-trichloro-2-hydroxypropyl)carbamate melting 100°–101° C.

EXAMPLE 5

To a stirred suspension of 5 grams of 3-(1,1-dimethylethylamino)-1,1,1-trichloro-2-propanol in 75 grams of dichloromethane at −60° C., 2.2 grams of acetic anhydride was added dropwise during 15 minutes. After the reaction mixture was allowed to warm to ambient temperature during 1 hour, the mixture was stirred for 2 hours. The solution was washed with 100 grams of saturated aqueous sodium bicarbonate, dried with anhydrous sodium sulfate and evaporated under a reduced pressure of 100 mm. Hg to 3.9 grams of an oil. The oil was crystallized from methylcyclohexane to yield 1.4 gram of white N-(1,1-dimethylethyl)-N-(3,3,3-trichloro-2-hydroxypropyl)acetamide melting 124°–126° C.

Useful formulations of the compounds of Formula (I) can be prepared in conventional ways. They include dusts, granules, solutions, suspensions, emulsions, wettable powders, emulsifiable concentrates and the like. Many of these may be applied directly. Alternatively, formulations which are to be sprayed can be extended in suitable media and used at spray volumes of from a few pints to several hundred gallons per acre. High strength compositions are primarily used as intermediates for further formulation. The formulations, broadly, can contain about 1% to 99% by weight of active ingredient(s) and at least one of (a) about 0.1% to 20% surfactant(s) and (b) about 5% to 99% solid or liquid inert diluent(s). More specifically, they will contain these ingredients in the following approximate proportions:

|  | Percent by Weight | | |
| --- | --- | --- | --- |
|  | Active Ingredient | Inert Diluent(s) | Surfactant(s) |
| Wettable Powders | 20–90 | 0–74 | 1–10 |
| Oil Suspensions, Emulsions, Solutions (including Emulsifiable Concentrates) | 5–50 | 40–95 | 0–15 |
| Aqueous Suspensions | 10–50 | 40–84 | 1–20 |
| Dusts | 1–25 | 70–99 | 0–5 |
| Granules | 1–95 | 5–99 | 0–15 |
| Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and can be achieved by incorporation into the formulation or by tank mixing.

Typical solid diluents are described in Watkins, et al., "Handbook of Insecticide Dust Diluents and Carriers", 2nd. Edn., Dorland Books, Caldwell, N.J. The more absorptive diluents are preferred for wettable powders and the denser ones for dusts. Typical liquid diluents and solvents are described in Marsden, "Solvents Guide", 2nd. Edn., Interscience, New York, 1950. Solubility under 0.1% is preferred for suspension concentrates; solution concentrates are preferably stable against phase separation at 0° C. "McCutcheon's Detergents and Emulsifiers Annual", Allured Publ. Corp., Ridgwood, New Jersey, as well as Sisely and Wood, "Encyclopedia of Surface Active Agents", Chemical Publ. Co., Inc., New York, 1964, list surfactants and recommended uses. All formulations can contain minor amounts of additives to reduce foam, corrosion, microbiological growth, etc.

The methods of making such compositions are well known. Solutions can be prepared by simply mixing the ingredients. Fine solid compositions can be made by blending and, usually, grinding as in a hammer or fluid energy mill. Suspensions can be prepared by wet milling. Granules may be made by spraying the active material upon preformed granular carriers or by agglomeration techniques.

The following examples further illustrate compositions of this invention.

EXAMPLE 6

| Wettable Powder | |
|---|---|
| 1-(1,1-dimethylethyl)-3-methyl-(3,3,3-trichloro-2-hydroxy-propyl)urea | 53% |
| sodium alkylnaphthalenesulfonate | 2% |
| sodium ligninsulfonate | 3% |
| diatomaceous earth | 42% |

The ingredients are blended and hammer-milled to produce particles of active essentially all below 50 microns in diameter. The product is reblended before packaging.

Alternatively, following hammer-milling the material may be air milled, to produce particles of active essentially all below 10 microns in diameter. The product is reblended before packaging.

EXAMPLE 7

| Wettable Powder | |
|---|---|
| 1-(1,1-dimethylethyl)-3-methyl-(3,3,3-trichloro-2-hydroxy-propyl)urea | 65% |
| dodecylphenol polyethylene glycol ether | 2% |
| sodium ligninsulfonate | 4% |
| sodium silicoaluminate | 6% |
| montmorillonite (calcined) | 23% |

The ingredients are thoroughly blended. The liquid surfactant is added by spraying upon the solid ingredients in the blender. After grinding in a hammer mill to produce particles practically all below 100 microns, the material is reblended and sifted through a U.S.S. No. 50 sieve (0.3 mm openings) and packaged.

EXAMPLE 8

| Oil Suspension | |
|---|---|
| 1-(1,1-dimethylethyl)-3-methyl-(3,3,3-trichloro-2-hydroxy-propyl)urea | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 9

| Solution | |
|---|---|
| 1-(1,1-dimethylethyl)-3-methyl-(3,3,3-trichloro-2-hydroxy-propyl)urea | 30% |
| dimethylformamide | 70% |

The ingredients are combined and stirred to produce a solution, which can be used for low volume applications.

EXAMPLE 10

| Emulsifiable Concentrate | |
|---|---|
| 1-(1,1-dimethylethyl)-3-methyl-(3,3,3-trichloro-2-hydroxy-propyl)urea | 20% |
| chlorobenzene | 74% |
| sorbitan monostearate and polyoxyethylene condensates thereof | 6% |

The ingredients are combined and stirred to produce a solution which can be emulsified in water for application.

EXAMPLE 11

| Aqueous Suspension | |
|---|---|
| 1-(1,1-dimethylethyl)-3-methyl-(3,3,3-trichloro-2-hydroxy-propyl)urea | 25% |
| hydrated attapulgite | 3% |
| crude calcium ligninsulfonate | 10% |
| sodium dihydrogen phosphate | 0.5% |
| water | 61.5% |

The ingredients are ground together in a ball or roller mill until the solid particles have been reduced to diameters under 10 microns.

EXAMPLE 12

| Aqueous Suspension | |
|---|---|
| 1-(1,1-dimethylethyl)-3-methyl-(3,3,3-trichloro-2-hydroxy-propyl)urea | 50.0% |
| polyacrylic acid thickener | 0.3% |
| dodecylphenol polyethylene glycol ether | 0.5% |
| disodium phosphate | 1.0% |
| monosodium phosphate | 0.5% |
| polyvinyl alcohol | 1.0% |
| pentachlorophenol | 0.4% |
| water | 46.3% |

The ingredients are ground together in a sand mill to produce particles essentially all under five microns in size.

EXAMPLE 13

| Dust | |
|---|---|
| 1-(1,1-dimethylethyl)-3-methyl-(3,3,3-trichloro-2-hydroxy-propyl)urea | 10% |
| attapulgite | 10% |
| talc | 80% |

The active ingredient is blended with attapulgite and then passed through a hammer mill to produce particles substantially all below 200 microns. The ground concentrate is then blended with powdered talc until homogeneous.

EXAMPLES 14

| High Strength Concentrate | |
| --- | --- |
| 1-(1,1-dimethylethyl)-3-methyl-(3,3,3-trichloro-2-hydroxypropyl)urea | 99% |
| trimethylnonyl polyethylene glycol ether | 1% |

The surfactant is sprayed upon the active ingredient in a blender and the mixture sifted through a U.S.S. No. 40 sieve (0.42 mm openings) prior to packaging. The concentrate may be formulated further for practical use.

EXAMPLE 15

| High Strength Concentrate | |
| --- | --- |
| 1-(1,1-dimethylethy)-3-methyl-(3,3,3-trichloro-2-hydroxypropyl)urea | 98.5% |
| silica aerogel | 0.5% |
| synthetic amorphous fine silica | 1.0% |

The ingredients are blended and ground in a hammer mill to produce a high strength concentrate essentially all passing a U.S.S. No. 50 sieve (0.3 mm openings). This material may then be formulated in any suitable way.

EXAMPLE 16

| Dust | |
| --- | --- |
| 1-(1,1-dimethylethyl)-3-methyl-(3,3,3-trichloro-2-hydroxypropyl)urea high strength composition from Example 14 or 15 | 25.4% |
| pyrophyllite, powdered | 74.6% |

The ingredients are thoroughly blended and packaged for use.

EXAMPLE 17

| Granule | |
| --- | --- |
| wettable powder of Example 6 or 7 | 10% |
| attapulgite granules (U.S.S. No. 20–40; 0.84–0.42 mm) | 90% |

A slurry of wettable powder containing 50% solids is sprayed on the surface of attapulgite granules in a double-cone blender. The granules are dried and packaged.

EXAMPLE 18

| Granule | |
| --- | --- |
| wettable powder of Example 6 | 15% |
| gypsum | 69% |
| potassium sulfate | 16% |

The ingredients are blended in a rotating mixer with a water spray to accomplish granulation. When most of the material has reached the desired range of 1.0 to 0.42 mm (U.S.S. No. 18 to 40 sieves), the granules are removed, dried, and screened. Oversize material is crushed to produce additional material in the desired size range. These granules contain about 7.5% active ingredient.

EXAMPLE 19

| Extruded Pellet | |
| --- | --- |
| 1-(1,1-dimethylethyl)-3-methyl-(3,3,3-trichloro-2-hydroxypropyl)urea | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

UTILITY

The compounds of this invention are effective for the control of plant diseases on a variety of host plants with a margin of plant safety. The diseases are incited by fungal pethogens represented by, but not limited to, *Phytophthora infestans, Uromyces phaseoli,* and *Puccinia graminis.*

Disease control is accomplished by applying an effective amount of the compounds of this invention to the portion of the plant to be protected such as the stems, foliage, fruit, seed or to the medium (soil) in which the plant is growing. Treatment may be prior to inoculation (preventive) or shortly after inoculation (curative).

Rates of application for compounds of this invention will be influenced by the specific host plants, the particular fungal pathogens, and many other factors of the environment and can be determined under the specific use conditions. However, foliage sprayed with concentrations ranging from 1 to 500 ppm active ingredient can usually be protected from disease under most conditions. Plants may also be protected from disease by treating the soil in which they are growing with the compounds of this invention at concentrations ranging from about 5 to 100 ppm by weight of the soil. Compositions of this invention may also contain conventional pesticides, such as insecticides, miticides, bactericides, nematicides, fungicides, or other agricultural chemicals such as growth modifying agents and fertilizer ingredients, and the like. The proper choice of conventional pesticide and their amounts can be made by one skilled in the art of protecting plants from pest depredation.

The following are illustrative of other fungicides that may be included in compositions or added to sprays containing one or more of the active compounds of this invention:

bis(dimethylthiocarbamoyl)disulfide; or tetramethylthiuram disulfide (thiram);
metal salts of ethylenebisdithiocarbamic acid or propylenebisdithiocarbamic acids. e.g., manganese, zinc, iron and sodium salts (maneb or zineb);
n-dodecylguanidine acetate (dodine);

N-(trichloromethylthio)phthalimide (folpet);
N-[(trichloromethyl)thio]-4-cyclohexene-1,2-discarboximide (captan);
cis-N-[(1,1,2,2-tetrachloroethyl)thio]-4-cyclohexene-1,2-dicarboximide (captafol);
2,4-dichloro-6-(o-chloroanilino)-α-triazine ("Dyrene");
3,3'-ethylenebis(tetrahydro-4,6-dimethyl-2H-1,3,5-thiadiazine-2-thione) (milneb);
triphenyltin hydroxide (fentin hydroxide);
triphenyltin acetate (fentin acetate);
N'-dichlorofluoromethylthio-N,N-dimethyl-N'-phenylsulfamide (dichlorofluanid);
tetrachloroisophthalonitrile (chlorothalonil);
tribasic copper sulfate;
fixed copper;
sulfur;
methyl 1-(butylcarbamoyl)-2-benzimidazolecarbamate (benomyl);
methyl 2-benzimidazolecarbamate (carbendazim);
1,2-bis(3-methoxycarbonyl-2-thioureido)-benzene (methyl thiophanate);
2-cyano-N-(ethylcarbamoyl)-2-methoxyimino acetamide N-(3',5'-dichlorophenyl)-1,2-dimethylcyclopropane-1,2-dicarboximide;
1-(4-chlorophenoxy)-3,3-dimethyl-1-(1H-1,2,4-triazol-1-yl)-2-butanone;
N-(2,6-dimethylphenyl)-N-(methoxyacetyl)-l-alanine methyl ester.

In the following examples of biological activity for the compounds of this invention percent disease control was calculated by the formula:

$$100 - \left[\frac{\text{disease rating on treated}}{\text{disease rating on untreated}}\right] \times 100 = \text{percent control}$$

All percentages are by weight unless otherwise indicated. Little or no plant injury was noted when host plants specified in the following examples were treated with compounds of this invention at the specified application rates. Exceptions are indicated after each Example.

EXAMPLE 20

Compounds of the invention were dissolved in acetone in an amount equal to 10% of the final volume and then suspended at a concentration of 80 ppm in purified water containing 250 ppm of the surfactant Trem ® 014 (polyhydric alcohol esters). This suspension was sprayed to the point of run-off on 6-week-old tomato plants. The following day the plants were inoculated with a spore suspension of *Phytophthora infestans* (Tomato Late Blight) and incubated in a saturated humidity chamber at 20° C. for 24 hours and then in a greenhouse for an additional 4 days when disease ratings were made. The results shown below indicate preventive action for plant disease control.

| Compound | Percent Control Tomato Late Blight |
| --- | --- |
| 1-(1,1-dimethylethyl)-3-methyl-1-(3,3,3-trichloro-2-hydroxypropyl)-urea | 100* |
| 1-(1,1-dimethylethyl)-3-methyl-1-[3,3,3-trichloro-2-(methylcarbamoxyloxy)-propyl]urea | 88* |
| N-(1,1-dimethyl-2-pro- | 90 |
| pynyl)-N'-methyl-N-(3,3,3-trichloro-2-hydroxypropyl)urea | |
| N-(1,1-dimethylethyl)-N-(3,3,3-trichloro-2-hydroxypropyl)acetamide | 88 |

*Foliage burn was associated with the chemical treatment.

EXAMPLE 21

Compounds of this invention were dissolved in acetone in an amount equal to 10% of the final volume and then suspended in purified water containing 250 ppm of the surfactant Trem ® 014 (polyhydric alcohol esters). This suspension was applied as a soil drench to tomatoes growing in soil at a rate of 25 kg/ha to the surface area. Twenty-four hours later, the plants were inoculated with a spore suspension of *Phytophthora infestans* and incubated in a saturated humidity chamber at 20° C. for 24 hours and then in a greenhouse for an additional 4 days when disease ratings were made. The results shown below indicate the systemic preventive action for plant-disease control.

| Compound | Percent Control Tomato Late Blight |
| --- | --- |
| 1-(1,1-dimethylethyl)-3-methyl-1-(3,3,3-trichloro-2-hydroxypropyl)urea | 100 |
| methyl(1,1-dimethylethyl)-(3,3,3-trichloro-2-hydroxypropyl)carbamate | 85* |
| N-(1,1-dimethyl-2-propynyl)-N'-methyl-N-(3,3,3-trichloro-2-hydroxypropyl)urea | 83* |
| N-(1,1-dimethylethyl)-N-(3,3,3-trichloro-2-hydroxypropyl)acetamide | 95 |

*Foliage burn was associated with chemical treatments.

EXAMPLE 22

1-(1,1-Dimethylethyl)-3-methyl-1(3,3,3-trichloro-2-hydroxypropyl)urea was dissolved in acetone in an amount equal to 10% of the final volume and then suspended at a concentration of 80 ppm in purified water containing 250 ppm of the surfactant Trem ® 014 (polyhydric alcohol esters). Six-week old tomato plants were inoculated with a spore suspension of *Phytophthora infestans* and incubated in a saturated humidity chamber at 20° C. for 6 hours and then allowed to dry before being sprayed to the point of run-off. The sprayed plants were placed back in the humidity chamber over night and then in the greenhouse for an additional 4 days when disease ratings were made. The plants treated with 1-(1,1-dimethylethyl)-3-methyl-1-(3,3,3-trichloro-2-hydroxypropyl)urea had only a few foliar lesions in contrast to untreated plants which had numerous leafspot lesions. 70 Percent disease control was recorded. There was some chemical burn on the tomato foliage associated with this treatment.

EXAMPLE 23

Compounds of this invention were dissolved in acetone in an amount equal to 10% of the final volume and then suspended at a concentration of 80 ppm in purified water containing 250 ppm of the surfactant Trem ® 014 (polyhydric alcohol esters). This suspension was sprayed to the point of run-off on wheat seedlings. The following day, the plants were inoculated with a spore suspension of *Puccinia graminis* var. *tritici* (Wheat Stem Rust) and incubated in a saturated humidity chamber at 20° C. for 24 hours and then in a greenhouse for an additional 7 days when disease ratings shown below were made. Percent preventive disease control is indicated below.

| Compound | Percent Control Wheat Stem Rust |
|---|---|
| 1-(1,1-dimethylethyl-3-methyl-1-(3,3,3-trichloro-2-hydroxypropyl)-urea | 100 |
| 1-(1,1-dimethylethyl)-3 methyl-1-[3,3,3-tri chloro-2-(methylcarbamoyl-oxy)propyl]urea | 87 |
| N-(1,1-dimethyl-2-propynyl)-N'-methyl-N-(3,3,3-tri-chloro-2-hydroxypropyl)urea | 85 |
| N-(1,1-dimethylethyl)-N-3,3,3-trichloro-2-hydroxy-propyl)acetamide | 95 |

EXAMPLE 24

1-(1,1-Dimethylethyl)-3-methyl-1-(3,3,3-trichloro-2-hydroxypropyl)urea was dissolved in acetone/DMF (9:1) solvent and applied to wheat seed as a seed coating treatment for systemic control of wheat stem rust caused by *Puccinia graminis* var. *tritici.* Treated seeds were allowed to dry, and then 10 seeds were planted per pot of sterile soil. The seeds were allowed to grow in normal greenhouse conditions, with temperatures ranging from 18°-25° C.

At 2 weeks of age, the seedlings from the treated seeds were inoculated with a spore suspension of *Puccinia graminis* var. *tritici* and incubated in a saturated humidity chamber at 20° C. for 24 hours and then in a greenhouse for an additional 7 days when disease ratings were made. Seedlings from seed treated at the rate of 2.5 grams of 1-(1,1-dimethyl-ethyl)-3-methyl-1-(3,3,3-trichloro-2-hydroxypropyl)urea per Kg of seed had only a few rust pustules (74% control) in contrast to untreated seed which produced plants having numerous rust pustules on each leaf.

EXAMPLE 25

1-(1,1-Dimethylethyl)-3-methyl-1-(3,3,3-trichloro-2-hydroxypropyl)urea was dissolved in acetone in an amount equal to 10% of the final volume and then suspended in purified water containing 250 ppm of the surfactant Trem ® 014 (polyhydric alcohol esters). To determine systemic effect, this suspension was applied as a soil drench to wheat plants at a rate of 5 kg/ha. Twenty-four hours later, the plants were inoculated with a spore suspension of *Puccinia graminis* tritici and incubated in a saturated humidity chamber at 20° C. for 24 hours and then in greenhouse for an additional 7 days when disease ratings were made. The plants grown in soil treated with 1-(1,1-dimethylethyl)-3-methyl-1-(3,3,3-trichloro-2-hydroxypropyl)urea had only a few rust pustules (95% control) in contrast to untreated plants which had numerous rust pustules on each leaf.

EXAMPLE 26

1-(1,1-Dimethylethyl)-3-methyl-1-(3,3,3-trichloro-2-hydroxypropyl)urea was dissolved in acetone in an amount equal to 10% of the final volume and then suspended at a concentration of 80 ppm in purified water containing the surfactant Trem ® 014 (polyhydric alcohol esters). This suspension was sprayed to the point of run-off on Pinto bean seedlings. The following day, the plants were inoculated with a spore suspension of the fungus *Uromyces phaseoli* var. *typica* (bean rust) and incubated in a saturated humidity chamber at 20° C. for 24 hours, and then in a greenhouse for an additional 7 days when disease ratings were made. Those bean plants treated with 1-(1,1-dimethylethyl)-3-methyl-1-(3,3,3-trichloro-2-hydroxypropyl)urea had few rust pustules (70% control) in contrast to untreated plants which had numerous rust pustules.

EXAMPLE 27

Compounds of this invention were dissolved in acetone in an amount equal to 10% of the final volume and then suspended in purified water containing 250 ppm of the surfactant, Trem ® 014 (polyhydric a alcohol esters). This suspension was applied as a soil drench to beans growing in soil at a rate of 25 Kg/Ha to surface area. Twenty-four hours later, the plants were inoculated with a spore suspension of *Uromyces phaseolic* var. *typica* and incubated in a saturated humidity chamber at 20° C. for 24 hours, and then in a greenhouse for an additional 7 days when disease ratings were made. Results of this test, shown below, indicate the systemic effect of these compounds.

| Compound | Percent Control Bean Rust |
|---|---|
| 1-(1,1-dimethylethyl)-3-methyl-1-(3,3,3-trichloro-2-hydroxy-propyl)urea | 100* |
| methyl(1,1-dimethyl-ethyl)-(3,3,3-tri-chloro-2-hydroxy-propyl) carbamate | 83 |
| N-(1,1-dimethylethyl)-N-(3,3,3-trichloro-2-hydroxypropyl)acetamide | 100* |

*Some foliage burn was associated with the chemical treatment.

EXAMPLE 28

1-(1,1-Dimethylethyl)-3-methyl-1-(3,3,3-trichloro-2-hydroxypropyl)urea was dissolved in acetone in an amount equal to 10% of the final volume and then suspended at a concentration of 80 ppm in purified water containing 250 ppm of the surfactant Trem ® 014 polyhydric alcohol esters). Pinto bean seedlings were inoculated with a spore suspension of *Uromyces phaseoli* var. *typica* (bean rust) and incubated in a saturated humidity chamber at 20° C. for 24 hours. After drying, the beans were sprayed to the point of run-off, the sprayed plants were placed back in the humidity chamber overnight and then in a greenhouse for an additional 7 days when disease ratings were made. The plants treated with 1-(1,1-dimethylethyl)-3-methyl-1-(3,3,3-trichloro-2-hydroxypropyl)urea had fewer rust pustules (67% control) in contrast to untreated plants which had numerous rust pustules.

What is claimed is:

1. A compound of the formula

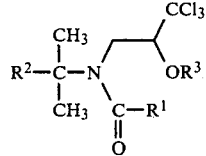

(I)

wherein
 $R^1$ is $CH_3NH$, $CH_3O$, or $CH_3$;
 $R^2$ is $CH_3$ or $HC\equiv C$; and
 $R^3$ is H or

provided that when $R^2$ is $HC\equiv C$, $R^1$ is $CH_3NH$ and $R^3$ is H; ps and provided that when $R^3$ is

$R^1$ is $CH_3NH$ and $R^2$ is $CH_3$.

2. A compound of claim 1 in which $R^2$ is $CH_3$.

3. A compound of claim 1 which is 1-(1,1-dimethylethyl)-3-methyl-(3,3,3-trichloro-2-hydroxypropyl)urea.

4. A composition consisting essentially of a fungicidally effective amount of a compound of claim 1 and at least one of (a) a solid or liquid inert diluent and (b) a surfactant(s).

5. A composition consisting essentially of a fungicidally effective amount of a compound of claim 2 and at least one of (a) a solid or liquid inert diluent and (b) a surfactant(s).

6. A composition consisting essentially of a fungicidally effective amount of a compound of claim 3 and at least one of (a) a solid or liquid inert diluent and (b) a surfactant(s).

7. A method for controlling fungus diseases of living plants which comprises applying to the locus to be protected a fungicidally effective amount of a compound of claim 1.

8. A method for controlling fungus diseases of living plants which comprises applying to the locus to be protected a fungicidally effective amount of a compound of claim 2.

9. A method for controlling fungus diseases of living plants which comprises applying to the locus to be protected a fungicidally effective amount of the compound of claim 3.

* * * * *